US007301043B2

(12) United States Patent
Deigner et al.

(10) Patent No.: US 7,301,043 B2
(45) Date of Patent: Nov. 27, 2007

(54) COMPOUNDS FOR DETERMINING THE ACTIVITY OF PHOSPHOLIPASE $A_2$

(75) Inventors: Hans-Peter Deigner, Lampertheim (DE); Stefan Russwurm, Jena (DE); Ralf Kinscherf, Schriesheim (DE); Wolfgang Lösche, Erfurt (DE)

(73) Assignee: Sirs-Lab GmbH, Jena (DE)

( * ) Notice: Subject to any disclaimer, the term of this patent is extended or adjusted under 35 U.S.C. 154(b) by 327 days.

(21) Appl. No.: 10/497,672

(22) PCT Filed: Oct. 23, 2002

(86) PCT No.: PCT/EP02/11852

§ 371 (c)(1),
(2), (4) Date: Oct. 15, 2004

(87) PCT Pub. No.: WO03/048172

PCT Pub. Date: Jun. 12, 2003

(65) Prior Publication Data

US 2005/0064532 A1    Mar. 24, 2005

(30) Foreign Application Priority Data

Dec. 7, 2001    (EP) ................... 01129137

(51) Int. Cl.
*C07F 9/02*    (2006.01)
(52) U.S. Cl. ........................ 558/175; 435/18
(58) Field of Classification Search ................ 558/175; 435/18
See application file for complete search history.

(56) References Cited

U.S. PATENT DOCUMENTS 6,146,625 A * 11/2000 Cousens et al. ............ 424/94.6
6,323,017 B1 * 11/2001 Adachi et al. .............. 435/195

FOREIGN PATENT DOCUMENTS

JP        4282391        7/1992

OTHER PUBLICATIONS

Hendrickson et al., "Intramolecularly Quenched BODIPY—Labeled Phospholipid Analogs in Phospholipase $A_2$ and Platelet—Activating Factor Acetylhydrolas Assays and in Vivo Fluorescene Imaging," Analytical Biochemistry, 276, pp. 27-35, Dec. 1, 1999.

Chihiro et al., "Preparation of phosphatidylethanolamine derivatives as substrates for phosphilipase $A_2$ determination," Chemical Abstracts, vol. 118, No. 19, 1 page, May 10, 1993.

Bayburt et al., "Continuous, Vesicle-Based Fluorimetric Assays of 14- and 85-kDa Phospilipases $A_2^1$," Analytical Biochemistry, 232, pp. 7-23, Nov. 20, 1995.

Thuren et al., "Phosphilipase A2 Assay Using an Intramolecularly Quenched Pyrene-Labeled Phospilipid Analog as a Substrate," Analytical Biochemistry, 170, pp. 248-255, Apr. 1988.

* cited by examiner

*Primary Examiner*—Ralph Gitomer
(74) *Attorney, Agent, or Firm*—Patterson, Thuente, Skaar & Christensen, P.A.

(57) ABSTRACT

Compounds for determining the activity of phospholipase $A_2$, are described herein, and include embodiments having formula (1)

$$F-L_1-O-CH_2 \atop HC-O-L_2-Q \atop H_2C-O-P(=O)(O^-)-O-(CH_2)_2-N^+(CH_3)_3 \tag{1}$$

wherein
$L_1$ is derived from an ether $(R^1-OR^2)_m$, wherein $R^1$ and $R^2$ are independently selected and are derived from a hydrocarbon having 1 to 12 carbon atoms, with m being an integer from 1 to 4, or from a hydrocarbon R having 1 to 20 carbon atoms;
F is unsubstituted or substituted pyrene as a flouraphore;
Q is a quencher, and
$L_2$ is $C(O)-L_1$ or $C(O)-L_1$-NH, wherein $L_1$ is as defined above. These compounds may be used to determine the activity of phospholipase $A_2$, in particular PAF-AH.

17 Claims, 1 Drawing Sheet

COMPOUNDS FOR DETERMINING THE ACTIVITY OF PHOSPHOLIPASE A$_2$

RELATED APPLICATION

This application claims priority to PCT Application No. PCT/EP02/11852 filed Oct. 23, 2002 and European Application No. 01129137.4 filed Dec. 7, 2001.

FIELD OF INVENTION

The invention relates to compounds which are suitable to determine the activity of phospholipase A$_2$ (PLA$_2$), in particular of Platelet-Activating Factor Acetylhydrolase (PAF-AH).

BACKGROUND

The Platelet-Activating Factor (PAF) is a biologically active phospholipid involved in physiological and pathophysiological processes. This factor is converted to biologically inactive products by a specific acetyl hydrolase, i.e. Platelet-Activating Factor Acetylhydrolase (PAF-AH, EC 3.1.1.47, also referred to as lipoprotein-associated phospholipase A$_2$), which cleaves off the acetate group at the sn-2 position. In addition to PAF, the substrate specificity also comprises oxidized phospholipids having polar substituents at the ω-position of the sn-2 ester. These altered substances are often found in oxidized lipoproteins. Since oxidized lipoproteins, in addition to PAF and oxidized phospholipids, also play a role in a great variety of diseases, it may be assumed that the enzyme also has a decisive influence on the genesis of said diseases.

SUMMARY OF THE INVENTION

In recent years, PAF-AH has become more and more important in research. In particular, abnormalities in PAF-AH activity have been found in a great variety of diseases. Series of clinical tests and the beginning of examinations of the enzyme, prepared in a recombinant manner, as a therapeutic agent (phase III of the clinical experiments will begin in early 2001 in the indicated field of sepsis (www.icos.com)) are showing its great importance for humans. Therefore, it is required to have a well-feasible method for determining the activity of PLA$_2$ in general and, in particular, of PAF-AH.

In order to determine the activity of PAF-AH, the literature describes a great variety of methods, such as radioactivity measurements, UV measurements or fluorescence measurements. In nearly all of these methods, the actual reaction of the substrate with a sample containing the enzyme is followed by one or more process step(s) (e.g. extraction, consequent reactions to indicators), so that continuous measurement of the enzyme kinetics is not possible.

The oldest and currently most widely used methods of determination are based on radioactivity measurements (M. E. Blank et al., J. Biol. Chem., 1981, 256, 175-178). These involve reacting a [$^3$H]-acetate-marked natural substrate with the sample to be investigated, whereby radioactively labeled acetic acid is cleaved off. After chromatographic processing of the test preparation, the cleaved-off acetic acid can be radioactively determined. However, chromatographic processing is time-consuming and, in part, also incurs high costs.

H. S. Hendrickson et al., Anal. Biochem., (1999), 276, 27-35 disclose intramolecularly quenched BODIPY-labeled phospholipid analogs in methods for determining PLA$_2$ and PAF-AH. One of said analogs is 1-(N-(BODIPY-FL-pentanoyl)-11-aminoundecyl)-2-((N-(2,4-dinitrophenyl) amino)-8-amino-octanoyl)-sn-glycero-3-phophocholine. BODIPY serves as a fluorophore.

However, this compound has quite severe drawbacks. Thus, the use of the aforementioned compound for determining the activity of PLA$_2$, in particular of PAF-AH, does not allow any statements as to changes of the lateral diffusion rate in membranes. Moreover, the properties of the aforementioned compound differ greatly from the properties of natural phospholipids.

Therefore, it is an object of the present invention to provide a means allowing to determine the activity of PLA$_2$, in particular of PAF-AH, without the disadvantages known from the prior art.

DETAIL DESCRIPTION OF THE PREFERRED EMBODIMENTS

According to the invention, this is achieved by a compound of formula (1)

wherein

L$_1$ is derived from an ether (R$^1$—OR$^2$)$_m$, wherein R$^1$ and R$^2$ are independently selected and are derived from a hydrocarbon having 1 to 12 carbon atoms, with m being an integer from 1 to 4, or from a hydrocarbon R having 1 to 20 carbon atoms;

F is unsubstituted or substituted pyrene as a fluorophore;

Q is a quencher, and

L$_2$ is C(O)-L$_1$ or C(O)-L$_1$-NH, wherein L$_1$ is as defined above.

Although the compounds of the invention comprise unsubstituted or substituted pyrene as a fluorophore, they are not fluorescent, because such fluorescence is quenched by the quencher which is also contained in the compound of the invention. Under the influence of PLA$_2$, in particular PAF-AH, the quencher is cleaved off and spatially separated from the remaining compound. This deactivates the quenching of fluorescence, so that an increase in fluorescence is observed. This increase in the intensity of fluorescence is generally directly proportional to the activity of PLA$_2$ and is thus an indicator for the activity of PLA$_2$, in particular of PAF-AH.

Surprisingly, it has been found that the use of the aforementioned compound for determining the activity of PLA$_2$, in particular of PAF-AH, allows statements to be made as to changes of the lateral diffusion rate in membranes. Moreover, the properties of the aforementioned compound differ greatly from the properties of natural phospholipids. Further, the compounds of the invention allow a determination of activity to be carried out in a particularly effective and easy manner. Activity can be measured in a direct and continuous manner.

As outlined above, unsubstituted or substituted pyrene is present as a fluorophore in the compound of the invention. Said fluorophore may be bound, via its 1-position, to L$_1$. If said pyrene is substituted, use is made of substituents which do not have a substantial influence on its properties as a fluorophore. Such substituents are known to the person skilled in the art. They may be amino groups or carbonyl groups or heteroatoms, such as N, S, or P, which substitute the C atoms of pyrene. The compound of the invention may comprise one or more independently selected substituents.

Compared with other fluorophores, such as NBD (N-(7-nitrobenz-2-oxa-1,3-diazole-4-yl)) or BODIPY (4,4-difluoro-4-bora-3a,4a-diaza-s-indacene), the above pyrenes have the advantages of a lower polarity, a great distance between the extinction wavelength and the emission wavelength, the ability to work in aqueous solution, a favourable distribution in cells, the ability to be incorporated in membranes without quenching of fluorescence as well as a pH-independent fluorescence. A further positive property of pyrenes is the formation of excimers at higher concentrations and a simultaneous shift of the emission wavelength to greater wavelengths. The formation of excimers allows an assessment of the concentration of the fluorophore.

According to the above formula (1), the compounds of the invention comprise a quencher. Quenchers are compounds known per se in the field of fluorescence, which reduce or extinguish the fluorescence intensity of the fluorophore. Examples of such quenchers include phenyl residues, which are substituted with one or more, in particular two, nitro groups, such as e.g. the 2,4-dinitrophenyl residue. These quenchers enable particularly efficient intramolecular reduction or quenching of the fluorescence intensity of the fluorophores.

In the compounds of the invention, the fluorophore is bound to the O atom at the sn 1 position of the glycerol via a linker. The quencher is also bound to the glycerol via a linker, namely at the sn-2 position of the glycerol. In doing so, the linkers are selected such, with regard to their dimensions, in particular their length, that optimal quenching of the fluorescence intensity can be observed. The linker $L_2$, by which the quencher is bound to the glycerol residue, is hydrolysable due to the O—C(O) group by $PLA_2$, in particular by PAF-AH. The quencher is cleaved off from the compound of the invention, together with the linker, by hydrolysis; the fluorescence intensity then increases, because intramolecular quenching is no longer possible. In contrast thereto, the linker L1, by which the fluorophore is bound to the glycerol, must not be cleaved off by $PLA_2$, in particular not by PAF-AH. Rather, the linker needs to be metabolically stable to detect the fluorescence intensity of the linkers.

As already outlined above, the linker may be derived from an ether $(R^1-OR^2)_m$, wherein $R^1$ and $R^2$ are independently selected and are derived from a hydrocarbon having 1 to 12 carbon atoms, with m being an integer from 1 to 4.

The term "hydrocarbons" relates to organic compounds consisting exclusively of carbon and hydrogen. Examples include alkanes, alkenes, and alkynes. Alkenes and alkynes may include several unsaturated bonds. According to the above formula (1), two H atoms of the aforementioned hydrocarbons are substituted so that they can perform their function as or in the linker. Said substitution may be effected, in particular, at terminal C atoms of the hydrocarbons.

In a preferred embodiment of the compound of the invention, $R^1$ and $R^2$ are $(CH_2)_n$, wherein n is an integer from 2 to 12. In particular, $L_1$ represents $(CH_2)_4$—O—$(CH_2)_{10}$. Linkers comprising $CH_2$ chains are especially favourable because they have particular metabolic stability, which ensures that the fluorophore remains in the compound of the invention, despite enzymatic treatment, and can be excited to fluoresce.

As outlined above, the linker $L_1$ may be derived from a hydrocarbon R. R is preferably $(CH_2)_o$, wherein o is an integer from 1 to 20, in particular 2 to 6. It has been found that linkers of this kind are particularly favourable, because they are metabolically stable, thus preventing any undesired cleavage of the fluorophore from the compound of the invention during treatment with enzymes.

The compound of the invention comprises a second linker $L_2$, by which the quencher is bound to the sn-2 position of the glycerol. As outlined above, $L_2$ is C(O)-L, or C(O)-$L_1$-NH, wherein $L_1$ is as defined above.

In a preferred embodiment, $L_2$ is $C(O)-(CH_2)_p$ or $C(O)-(CH_2)_p$—NH, wherein p is an integer from 1 to 20, in particular 2 to 6, and, in particular, L2 means $C(O)-(CH_2)_5$—NH. These linkers are particularly well-suited because, on the on hand, the CH2 chain is metabolically stable, thus avoiding undesired cleavage of the quencher at this location, and, on the other hand, the ester group —C(O)—O— of $PLA_2$, in particular of PAF-AH, is purposefully and selectively cleaved by these enzymes.

One advantage of pyrene binding to the 1-position of glycerol is that it is metabolically stable there; no disruptions of the test by phospholipase A1 activities, which may also be present in the sample to be investigated, are observed.

The phosphatidylcholine residue is present at the sn 3-position of glycerol. This favourably ensures that the compounds of the invention exhibit the biophysical behaviour of natural phospholipids.

In a particularly preferred embodiment, the compound of the invention has a structure of formula (2)

(2)

This compound of the invention according to formula (2) enables measurement of the activity of $PLA_2$, in particular of PAF-AH, in a particularly easy and favourable manner.

In order to prepare the compound of the invention, the skilled person can resort to conventional reactions and methods in synthetic organic chemistry. For example, the fluorophore may first be bound to a linker, then the second end of the linker can be introduced at the sn-1 position of the glycerol. The phosphocholine residue may then be introduced at the sn-3 position of the glycerol, wherein the OH group at the sn-2 position of the glycerol may be protected by a protective group, for example by a benzoyl group. The protective group may be subsequently cleaved off in a conventional manner, and then the second linker may be inserted, optionally together with the quencher. The method of preparing the compounds of the invention was described above without a detailed description of intermediate steps. For example, insertion of the linker into the fluorophore may be effected in several steps, such as those described, e.g., in the preparation example below.

The presence of the quencher in the compound of the invention causes intramolecular quenching of fluorescence. By cleaving off the quencher from the compound of the invention, intramolecular quenching is no longer possible, so that an increase in the fluorescence intensity of the fluorophore is observed. Such cleavage of the quencher from the compound of the invention may be effected by means of $PLA_2$, in particular PAF-AH, namely by hydrolysis of the ester group at the sn-2 position. The compounds of the invention are, therefore, particularly well-suited to determine the activity of $PLA_2$, in particular of PAF-AH.

In such a method of determining the activity of $PLA_2$, in particular of PAF-AH, a sample containing said enzyme is incubated with the compound of the invention and fluorescence is measured in a conventional manner. In doing so, incubation is favourably effected under physiologic conditions, for example at pH 7.4 in an aqueous medium, e.g. buffer, and at 37° C., so as to enable measurement of the activity of the enzyme in an environment which is as natural as possible. The measurement of fluorescence, i.e. the increase in fluorescence, may be effected in a continuous manner. Such continuous measurement allows fluorescence to be permanently determined over a longer period of time from a few minutes to several hours, in particular from 5 minutes to 0.5 hours.

The compounds of the invention are, therefore, particularly well-suited to determine the enzymes $PLA_2$, in particular PAF-AH. These compounds enable particularly effective, direct, easy, quick and low-cost measurement. Furthermore, said activity measurement can be carried out in a continuous manner, i.e. over a longer period of time, thus allowing to obtain valuable information in relation to enzyme kinetics. Moreover, using the compounds of the invention very exact values are obtained, which allow the reliable statements to be made, in particular for therapeutic and diagnostic purposes.

The activity measurement of enzymes may have a large number of applications, for example as a diagnostic agent for differential diagnosis of a great variety of biological samples in humans and animals (nose secretion, sperm, lung secretion (BAL), blood or its constituents, isolated cell populations, tissue biopsies, gall secretion, intestinal secretion, stool specimens, such as to detect a great variety of metabolic functions, e.g. unspecific conditions, such as hyperlipidemia, conditions of increased oxidative stress, for the diagnose of acute inflammatory diseases, such as sepsis, ARDS (lung failure), as well as inflammations of solitary organs as well as, in particular, also of wound-healing disorders;

to detect chronic inflammatory conditions, such as rheumatoid arthritis, and further diseases of the rheumatic type, Colitis ulzerosa, Morb. Crohn;

in other local and systemic inflammatory conditions;

in allergy—and/or immunology-mediated diseases, e.g. allergies to pollen and to latex, glomerulonephritis;

in diseases of the toxic genesis, e.g. toxic lung failure or poisoning conditions;

in coronary diseases, e.g. acute coronary syndrom, angina pectoris, Prinzmetal's angina, cardiac infarction, as well as arteriosclerosis, acute cerebral insult;

in other conditions, such as after transplantations, operations, other invasive procedures;

in connection with medical check-ups for the above-mentioned medical syndromes;

for therapy monitoring of medical measures, such as any kind of medicinal intervention, such as therapies using recombinant enzymes, as well as all types of therapeutic intervention involving changes in the activity of the corresponding enzymes; in particular, in the above-mentioned fields of therapeutic indication;

invasive measures, such as operations for removal of inflammatory causes, operations including replacement or mechanical support of the heart-lung function, operations on the liver and also a great variety of transplantations; in particular, in the above-mentioned fields of therapeutic indication;

the combination of both.

Determining the activity of $PLA_2$, in particular of PAF-AH, using the compounds of the invention, has a great number of advantages. Thus, the activity of the enzyme can be determined without burdensome process steps and without side reactions. The addition of suitable inhibitors enables selective measurement of enzymes cleaving phospholipid esters in mixtures of various hydrolases. The determination of enzyme activity using the compounds of the invention may be effected in the wells of microtiter plates. Further, this determination of activity is suitable for HTS. The continuous measurement enables detection of kinetic data, such as IC50 and KI values.

Figure 1:
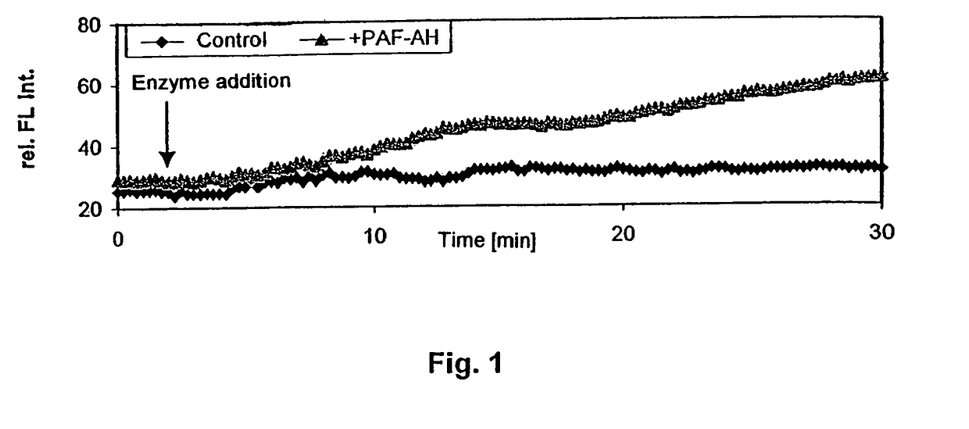
FIG. 1 shows the time course of the increase in fluorescence by the effect of PAF-AH on the 1-O-{10-[4-(pyrene-1-yl)-butoxy]-decyl}-2-(6-(2,4-dinitrophenyl)-aminohexoyl)-rac-glycero-3-phos-phocholine compound according to the invention. The measurement was carried out under the conditions described above. As is apparent from FIG. 1, an increase in fluorescence occurs in the presence of PAF-AH. No increase in the intensity of fluorescence was observed without PAF-AH (control).
Figure 2:
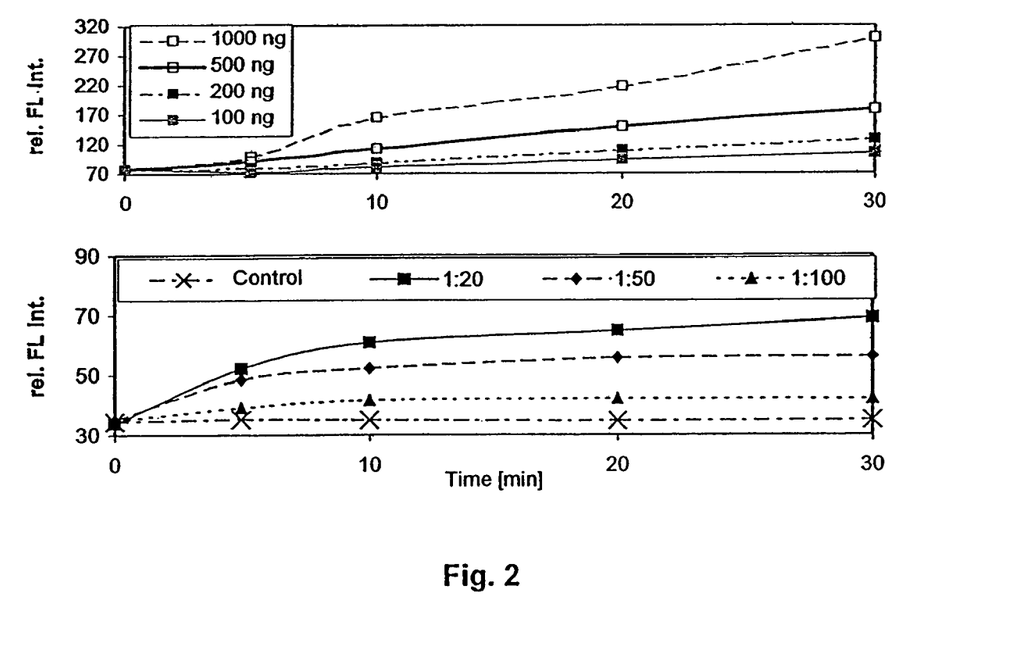
FIG. 2 shows the connection between different amounts of PAF-AH or different dilutions of human sample material and the increase in the intensity of fluorescence (test conditions as above). It was found that a marked increase in the intensity of fluorescence can be observed at higher PAF-AH concentrations.

The following examples explain the present invention without limiting it thereto, however, with reference to FIGS. 1 and 2, wherein

FIG. 1 shows the typical time course of the increase in fluorescence due to the effect of PAF-AH, and FIG. 2 shows the relationship between different amounts of enzyme or different dilutions of human sample material and the increase in fluorescence.

EXAMPLE 1

Preparation of 1-O-{(10-[4-(pyrene-1-yl)-butoxy]-decyl}-2-(6-(2,4-dinitrophenyl)-aminohexoyl-rac-glycero-3-phosphocholine According to the invention Dichloro-phosphoric acid-(2-bromoethylester)

To a solution of 42.5 g (0.275 mol) of phosphoryl chloride in 50 ml of dichloromethane, 27 g (0.215 mol) of bromoethanol in 15 ml of dichloromethane were added dropwise within 15 min at room temperature. After 15 min, a slight argon stream was passed through the reaction solution for 18 hours. Destillation in an oil pump vacuum (73-74° C., 3*10$^{-2}$ mbar) yielded 50.5 g (76%) of a colorless liquid.

M (C$_2$H$_4$$^{79}$Br$^{35}$Cl$_2$O$_2$$^{31}$P)=239 g/mol

EI-MS: m/z (%)=243 (0.5) [M], 241 (0.9) [M], 239 (0.6) [M], 163 (25), 161 (41), 149 (18), 147 (30), 137 (36), 135 (55), 119 (23), 117 (34), 109 (64), 108 (100), 107 (69), 106 (100), 99 (18), 47 (27). $^1$H-NMR (CDCl$_3$): δ (ppm)=4.59 (2H, m, CH$_2$Br, $^3J_{HH}$=6.26 Hz, $^3J_{HP}$=10.34 Hz), 3.13 (2H, m, CH$_2$O, $^3J_{HH}$=6.26 HZ, $^4J_{HP}$=1.05 Hz). $^{13}$C-NMR (CDCl$_3$): δ (ppm)=69.88 (1 CH$_2$O, $^2J_{CP}$=8.39 Hz), 27.32 (1 CH$_2$Br, $^3J_{CP}$=10.29 Hz). IR (Film): ν (cm$^{-1}$)=3033w, 2971w, 2883w, 1453m, 1423m, 1385m, 1306s, 1233m, 1180m, 1071s, 1016s, 963m, 908m, 845w, 759m.

4oxo-4-(pyrene-1-yl)-butyric acid

To a solution of 0.5 g (5 mmol) of succinic anhydride in 60 ml of nitrobenzene, 1.32 g (5 mmol) of anhydrous AlCl$_3$ and 1 g (5 mmol) of pyrene were added at 0° C. After a reaction time of 18 hours at room temperature, the solution was poured onto 30 ml of iced hydrochloric acid (25%), forming a precipitate. Filtration and recrystallization from EtOH yielded 1.233 g (82%) of 4-oxo-4-(pyrene-1-yl)-butyric acid.

M (C$_{20}$H$_{14}$O$_3$)=302 g/mol

EI-MS: m/z (%)=303 (10) [MH$^+$], 302 (42) [M], 230 (16), 229 (100), 202 (11), 201 (65), 200 (24). HR-EI-MS (C$_{20}$H$_{14}$O$_3$) calc.: 302.0943; found: 302.0943. $^1$H-NMR ([D$_6$]-DMSO): δ (ppm)=8.81-8.12 (9H, m, CH$_{arom}$), 3.52 (2H, t, COCH$_2$, $^3J_{HH}$=6.22 Hz), 2.82 (2H, t, CH$_2$CO$_2$H, $^3J_{HH}$=6.22 Hz). $^{13}$C-NMR ([D$_6$]-DMSO): δ (ppm)=203.05 (1 CO), 173.87 (1 CO$_2$H), 132.97-123.41 (9 CH$_{arom}$, 7 C$_{arom}$), 36.87 (1 COCH$_2$), 28.52 (1 CH$_2$CO$_2$H). IR (KBr): ν (cm$^{-1}$)=3426m, 3039m, 2984m, 2929m, 2677w, 2594w, 1695s, 1665s, 1507w, 1404w, 1212m, 1123m, 1075w, 842m, 713w.

4-(pyrene-1-yl)-butyric acid 1 g (2.78 mmol) of 4-oxo-4-(pyrene-1-yl)-butyric acid was dissolved in 30 ml diethylene glycol and 0.5 9 (10 mmol) of hydrazine hydrate as well as 0.56 g (10 mmol) of KOH added thereto. The reaction solution was heated under reflux for 2 hours and then poured onto iced hydrochloric acid (25%), forming a yellow precipitate. Filtration of the solid and recrystallization from EtOH yielded 570 mg (71%) of 4-(pyrene-1-yl)-butyric acid.

M (C$_{20}$H$_{16}$O$_2$)=288 g/mol

EI-MS: m/z (%)=289 (16) [MH$^+$], 288 (62) [M], 216 (20), 215 (100), 213 (11). HR-EI-MS C$_{20}$H$_{16}$O$_2$): calc.: 288.1150; found: 288.1150. $^1$H-NMR ([D$_6$]-DMSO): δ (ppm)=8.50-7.92 (9H, m, CH$_{arom}$), 3.36 (2H, m, CH$_2$C$_{16}$H$_9$), 2.41 (2H, m, CH$_2$CO$_2$H), 2.04 (2H, m, CH$_2$). $^1$H-NMR (CDCl$_3$): δ (ppm)=8.32-7.86 (9H, m, CH$_{arom}$), 3.42 (2H, t, CH$_2$C$_{16}$H$_9$, $^3J_{HH}$=7.57 Hz), 2.51 (2H, t, CH$_2$CO$_2$H, $^3J_{HH}$=7.00 Hz), 2.23 (2H, m, CH$_2$, $^3J_{HH}$=7.57 Hz, $^3J_{HH}$=7.00 Hz). $^{13}$C-NMR ([D$_6$]-DMSO): δ(ppm)=174.74 (1 CO), 136.39-123.39 (9 CH$_{arom}$, 7 C$_{arom}$), 33.64-26.98 (1 CH$_2$CO$_2$H, 2 CH$_2$). $^{13}$C-NMR (CDCl$_3$): δ (ppm)=177.48 (1 CO), 135.25-123.04 (9 CH$_{arom}$, 7 C$_{arom}$), 33.21-26.46 (1 CH$_2$CO$_2$H, 2 CH$_2$). IR (KBr): ν (cm$^{-1}$)=3447w, 3037w, 2950m, 2934w, 2874w, 1695s, 1431w, 1275m, 1206w, 918w, 846s, 711w.

4-(pyrene-1-yl)-butyric acid methylester

To 40 ml of methanol, 20 ml (260 mmol) of thionyl chloride were dropwise added at 0° C. Then, the solution was stirred at room temperature for 1 h. After addition of 5.50 g (19 mmol) of 4-(pyrene-1-yl)-butyric acid, the preparation was stirred over night at room temperature. The reaction was neutralized with saturated NaHCO$_3$ solution and extracted with acetic acid ethylester. An aliquot was taken from the organic phase for analysis. The remainder of the crude product was used further to prepare 4-(pyrene-1-yl)-butane-1-ol.

M (C$_{21}$H$_{18}$O$_2$)=302 g/mol

EI-MS: m/z (%)=303 (13) [MH$^+$], 302 (57) [M], 228 (15), 216 (22), 215 (100), 213 (12), 108 (13). HR-EI-MS (C$_{21}$H$_{18}$O$_2$): calc.: 302.1307; found: 302.1306. $^1$H-NMR (CDCl$_3$): δ (ppm)=8.25-7.70 (9H, m, CH$_{arom}$), 3.63 (3H, s, CH$_3$), 3.27 (2H, t, CH$_2$C$_{16}$H$_9$, $^3J_{HH}$=7.60 Hz), 2.36 (2H, t, CH$_2$CO, $^3J_{HH}$=7.20 Hz), 2.11 (2H, m, CH$_2$, $^3J_{HH}$=7.20 Hz, $^3J_{HH}$=7.60 Hz). $^{13}$C-NMR (CDCL$_3$): δ (ppm)=173.73 (1 CO), 135.51-123.15 (9 CH$_{arom}$, 7 C$_{arom}$), 51.38 (1 CH$_3$), 33.52-26.64 (1 CH$_2$CO, 2 CH$_2$). IR (KBr): ν (cm$^{-1}$)=3033w, 2949m, 2876w, 1734s, 1429m, 1209m, 1161m, 842s.

4-(pyrene-1-yl)-butane-1-ol

The crude product from the previous step was dissolved in 30 ml of THF at 0° C., with 3 g (79 mmol) of LiAlH$_4$ being added thereto. The reaction was stirred over night at room temperature. Then, excessive reducing agent was hydrolysed. Column chromatography yielded 4.6 g (92%, in 2 steps) of the desired compound.

M (C$_{20}$H$_{18}$O)=274 g/mol

EI-MS: m/z (%)=275 (10) [MH⁺], 274 (53) [M], 216 (17) 215 (100). HR-EI-MS (C$_{20}$H$_{18}$O): calc.:274.1358; found: 274.1357. $^1$H-NMR (CDCl$_3$): δ (ppm)=8.23-7.79 (9H, m, CH$_{arom}$), 3.64 (2H, t, CH$_2$O, $^3J_{HH}$=6.39 Hz), 3.31 (2H, t, CH$_2$C$_{16}$H$_9$, $^3J_{HH}$=7.60 Hz), 187 (2H, m, CH$_2$, $^3J_{HH}$=7.70 Hz, $^3J_{HH}$=7.60 Hz), 1.69 (2H, m, CH$_2$, $^3J_{HH}$=7.70 Hz, $^3J_{HH}$=6.39 Hz). $^{13}$C-NMR (CDCl$_3$): δ (ppm)=136.65-123.35 (9 CH$_{arom}$, 7 C$_{arom}$), 62.77 (1 CH$_2$O), 33.17-27.93 (3 CH$_2$). IR (KBr): ν (cm$^{-1}$)=3423s, br, 3038m, 2927m, 2859m, 1181w, 1030w, 982w, 841s.

1-[4-(10-bromo-decyloxy)-butyl]-pyrene 2 g (7.3 mmol) of 4-(pyrene-1-yl)-butane-1-ol were heated at 100° C. for 1 hour in 50 ml of toluene containing 1 g (9 mmol) of potassium-tert-butylate. Then, 2.22 g (7.4 mmol) of 1,10-dibromodecane were added and heated for 16 further hours. Column chromatography yielded 2.82 g (79%) of a light yellow solid.

M (C$_{30}$H$_{37}$O$^{78}$Br)=492 g/mol

EI-MS: m/z (%)=495 (10) [MH⁺], 494 (31) [M], 493 (10) [MH⁺], 492 (33) [M], 412 (13), 228 (22), 215 (100), 55 (18), 41 (13). HR-EI-MS (C$_{30}$H$_{37}$O$^{78}$Br): calc.: 492.2028; found: 492.2028. $^1$H-NMR (CDCl$_3$): δ (ppm)=8.30-7.85 (9H, m, CH$_{arom}$), 3.49-3.45 (2H, t, CH$_2$Br, $^3J_{HH}$=6.44 Hz), 3.41-3.34 (6H, m, CH$_2$C$_{16}$H$_9$, 2 CH$_2$O, $^3J_{HH}$=7.08 Hz, $^3J_{HH}$=6.81 Hz), 1.96-1.90 (2H, m, CH$_2$, $^3J_{HH}$=7.08 Hz, $^3J_{HH}$=6.44 Hz), 1.83-1.73 (4H, m, 2 CH$_2$, $^3J_{HH}$=6.81 Hz), 1.55-1.53 (2H, m, CH$_2$), 1.25 (12H, m, 6 CH$_2$). $^{13}$C-NMR (CDCl$_3$): δ (ppm)= 136.72-123.30 (9 CH$_{arom}$, 7 C$_{arom}$), 70.93-70.55 (2 CH$_2$O), 33.94-26.15 (1 CH$_2$Br, 11 CH$_2$). IR (KBr): ν (cm$^{-1}$)=3037w, 2924s, 2851s, 1499m, 1448m, 1429w, 1369w, 1243w, 1184w, 1117s, 1063w, 965w, 849m, 841s, 710s.

2,2-dimethyl-4-[10-O-(4-(pyrene-1-yl)-butoxy)decyl)-methyl]-[1,3]-dioxolane 1.85 g (14 mmol) of 2,2-Dimethyl-4-hydroxymethyl-1,3-dioxolan were heated with reflux for 1 hour in 80 ml of toluene containing 1.6 g (14 mmol) of potassium-tert-butylate. After cooling to room temperature, 2.118 g (4.3 mmol) of 1-[4-(10-bromo-decyloxy)-butyl]-pyrene were added and heated for 18 further hours. Column chromatography yielded 1.174 g (50%) of a light yellow solid., M (C$_{36}$H$_{48}$O$_4$)=544 g/mol EI-MS: m/z (%)=545 (22) [MH⁺], 544 (62) [M], 257 (22), 228 (24), 216 (22), 215 (100), 101 (18), 55 (11), 43 (14). HR-EI-MS (C$_{36}$H$_{48}$O$_4$): calc.: 544.3553; found: 544.3553. $^1$H-NMR (CDCl$_3$): δ (ppm)=8.29-7.83 (9H, m, CH$_{arom}$), 4.26-4.21 (2H, m, CHCH$_2$O), 4.07-4.00 (1H, m, CHO), 3.75-3.31 (10H, m, 4 OCH$_2$, CH$_2$C$_{16}$H$_9$), 1.95-1.86 (2H, m, CH$_2$), 1.78-1.72 (2H, m, CH$_2$), 1.55-1.53 (4H, m, CH$_2$), 1.41 und 1.35 (6H, s, 2 CH$_3$), 1.26 (12H, m, 6 CH$_2$). $^{13}$C-NMR (CDCl$_3$): δ (ppm)=136.92-123.48 (9 CH$_{arom}$, 7 C$_{arom}$), 109.33 (1 C(CH$_3$)$_2$), 74.77 (1 CHO), 71.85-70.64 (4 CH$_2$O), 66.94 (1 CH$_2$O), 33.33-25.89 (11 CH$_2$), 26.77 und 25.43 (2 CH$_3$). IR (KBr): ν (cm$^{-1}$)=3059m, 2952s, 2890m, 2866s, 1524w, 1467m, 1369w, 1289m, 11121m, 1058m, 837w, 684s.

1-O-{10-[4-(pyrene-1-yl)-butoxy]-decyl}-rac-glycerol 1 ml trifluoroacetic acid was added to 0.183 g (0.336 mmol) of 2,2-dimethyl-4-[10-O-(4-(pyrene-1-yl)-butoxy)-decyl)-methyl]-[1,3]-dioxolane in 10 ml of toluene at 0° C. and stirred for one hour. After neutralization with an aqueous solution of NaHCO$_3$, column chromatography yielded 0.160 g (94%) of a light yellow solid.

M (C$_{33}$H$_{44}$O$_4$)=504 g/mol

EI-MS: m/z (%)=505 (32) [MH⁺], 504 (100) [M], 257 (17), 228 (21), 216 (19), 215 (89), 55 (14). HR-EI-MS (C$_{33}$H$_{44}$O$_4$): calc.: 504.3240; found: 504.3238. $^1$H-NMR (CDCl$_3$); δ (ppm)=8.29-7.83 (9H, m, CH$_{arom}$), 3.87-3.59 (3H, m, CHOH, CH$_2$OH), 3.47-3.31 (10H, m, 4 OCH$_2$, CH$_2$C$_{16}$H$_9$), 1.94-1.89 (2H, m, CH$_2$), 1.77-1.72 (2H, m, CH$_2$), 1.54-1.51 (4H, m, 2 CH$_2$), 1.24 (12H, m, 6 CH$_2$). $^{13}$C-NMR (CDCl$_3$): δ (ppm)=136.94-123.48 (9 CH$_{arom}$, 7 C$_{arom}$), 72.03-70.65 (4 CH$_2$O), 70.50 (1 CHOH), 63.81 (1 CH$_2$OH), 33.31-25.97 (11 CH$_2$). IR (KBr): ν (cm$^{-1}$)=3419s, br, 3058w, 2932m, 2851m, 1437m, 1433m, 1265m, 1205m, 1186m, 1138m, 1112m, 1048m, 843m.

1-O-{10-[4-(pyrene-1-yl)-butoxy]-decyl}-3-O-triphenylmethyl-rac-glycerol 4.215 g (8.4 mmol) of 1-O-{10-[4-(pyrene-1-yl)-butoxy]-decyl}-rac-glycerol were prepared in 50 ml of acetonitrile, to which 4.09 g (10 mmol) of 1-(triphenylmethyl)pyridinium-tetrafluoroborate were added in 20 ml of acetonitrile. The solution was stirred for 18 hours, concentrated and taken up by chloroform. The solid was filtered off. Column chromatography of the filtrate yielded 3.697 g (59%) of the desired compound as a light yellow solid.

M (C$_{52}$H$_{58}$O$_4$)=746 g/mol

FAB-MS (FAB⁺, NBA): m/z=746.4 [M], 504.3, 244.1, 215.1. HR-FAB (C$_{52}$H$_{58}$O$_4$) calc.: 746.4335 found: 746.4375. HR-FAB (C$_{52}$H$_{58}$O$_4$Na): calc.: 769.4233; found: 769.4304. $^1$H-NMR (CDCl$_3$): δ (ppm)=8.31-7.85 (9H, m, CH$_{arom}$), 7.45-7.19 (15H, m, CH$_{arom}$), 3.95 (1H, m, CH), 3.55-3.33 (10H, m, 4 OCH$_2$, CH$_2$C$_{16}$H$_9$), 3.24-3.18 (2H, m, CH$_2$OC(C$_6$H$_5$)$_3$), 1.97-1.87 (2H, m, CH$_2$), 1.81-1.73 (2H, m, CH$_2$), 1.55-1.51 (4H, m, 2 CH$_2$), 1.25 (12H, m, 6 CH$_2$). $^{13}$C-NMR (CDCl$_3$): δ (ppm)=146.90-123.51 (24 CH$_{arom}$, 10 C$_{arom}$), 86.65 (1 C(C$_6$H$_5$)$_3$), 72.95-70.67 (4 CH$_2$O), 69.87 (1 CH), 64.65 (1 CH$_2$OC(C$_6$H$_5$)$_3$), 33.35-26.97 (11 CH$_2$). IR (KBr): ν (cm$^{-1}$)=3429m, 3056w, 2927s, 2855s, 1602w, 1490m, 1448m, 1319w, 1213m, 1113m, 1077m, 1033m, 899w, 846m, 746m, 706s.

1-O-{10-[4-(pyrene-1-yl)-butoxy]-decyl}-2-O-benzoyl-3-O-triphenylmethyl-rac-glycerol To a solution of 2.578 g (3.455 mmol) of 1-O-{10-[4-(pyrene-1-yl)-butoxy]-decyl}-3-O -triphenylmethyl-rac-glycerol and 1.5 ml (18.66 mmol) of pyridine in 50 ml of $CH_2Cl_2$, 540 mg (3.857 mmol) of benzoylchloride were added dropwise at 0° C. Benzoylchlorid and stirred at room temperature for 1 hour. After column chromatography, 2.8 g (95%) of the product were isolated.

M ($C_{59}H_{62}O_5$)=850 g/mol

FAB-MS (FAB⁺, NBA): m/z=873.4 [M+Na], 850.4 [M], 608.3, 591.3, 391.3, 307.1, 243.1, 215.1. ¹H-NMR (CDCl₃): δ (ppm)=8.30-7.86 (9H, m, $CH_{arom}$), 7.45-7.21 (20H, m, $CH_{arom}$), 5.46-5.41 (1H, m, CH), 3.79-3.34 (12H, m, 4 $CH_2O$, $CH_2C_{16}H_9$, $CH_2OC(C_6H_5)_3$), 1.97-1.89 (2H, m, $CH_2$),1.80-1.72 (2H, m, $CH_2$), 1.55-1.51 (4H, m, $CH_2$), 1.25 (12H, m, $CH_2$). ¹³C-NMR (CDCl₃): δ(ppm)=166.00 (1 CO), 146.88-123.51 (29 $CH_{arom}$, 11 $C_{arom}$), 86.47 (1 $C(C_6H_5)_3$), 72.65 (1 CH), 71.59-69.47 (4 $CH_2O$), 62.86 (1 $CH_2OC(C_6H_5)_3$), 33.35-26.01 (11 $CH_2$). IR (KBr): ν (cm⁻¹)= 3057w, 2927s, 2854m, 1718s, 1448m, 1384m, 1272m, 1212w, 1177w, 1158w, 1112m, 1032w, 899w, 846m, 763m, 703m.

1-O-{10-[4-(pyrene-1-yl)-butoxy]-decyl}-2-O-benzoyl-rac-glycerol 0.55 g (0.647 mmol) of 1-O-{10-[4-(pyrene-1-yl)-butoxy]-decyl}-2-O-benzoyl-3-O -tri-phenylmethyl-rac-glycerol were dissolved in 20 ml $CH_2Cl_2$, and 0.5 ml BF₃ (13% in MeOH) was added dropwise thereto at −10° C. The reaction was stopped with 5 ml of iced water after one hour. Column chromatography yielded 280 mg (71%) of the compound.

M ($C_{40}H_{48}O_5$)=608 g/mol

FAB-MS (FAB⁺, NBA): m/z=608.3 [M], 591.3, 469.3, 329.1, 257.2, 215.1. HR-FAB ($C_{40}H_{48}O_5$): calc.: 608.3502; found: 608.3519. HR-FAB ($C_{40}H_{48}O_5Na$): calc.: 631.3399; found: 631.3424. ¹H-NMR (CDCl₃): δ (ppm)=8.29-7.84 (9H, m, $CH_{arom}$), 7.62-7.34 (5H, m, $CH_{arom}$), 5.27-5.22 (1H, m, CH), 3.99-3.34 (12H, m, 4 $CH_2O$, $CH_2C_{16}H_9$, $CH_2OH$), 1.97-1.88 (2H, m, $CH_2$), 1.80-1.72 (2H, m, $CH_2$), 1.57-1.51 (4H, m, 2 $CH_2$), 1.25 (12H, m, 6 $CH_2$). ¹³C-NMR (CDCl₃): δ (ppm)=166.38 (1 CO), 136.94-123.51 (14 $CH_{arom}$, 8 $C_{arom}$), 73.81 (1 CH), 71.94-68.95 (4 $CH_2O$), 62.87 (1 $CH_2OH$), 33.80-26.19 (11 $CH_2$). IR (KBr): ν (cm⁻¹)= 3431m, 3038m, 2930s, 2859m, 1718s, 1603m, 1585m, 1453m, 1435m, 1317m, 1274s, 1179m, 1113m, 1027m, 936m, 846m, 709s.

1-O-{-10-[4-(pyrene-1-yl)-butoxy]-decyl}-2-O-benzoyl-rac-glycero-3-phosphocholine

0.55 g (2.3 mmol) of 2-bromoethyl-dichlorophosphate were added to 15 ml of $CH_2Cl_2$ at 0° C., and a mixture of 1.6 ml of pyridine and 4 ml of $CH_2Cl_2$ was added dropwise thereto. Then, 210 mg (3.45 mmol) of 1-O-{10-[4-(pyrene-1-yl)-butoxy]-decyl}-2-O-benzoyl-rac-glycerol were dissolved in 2 ml of $CH_2Cl_2$ and added dropwise to the phosphorylation mixture at room temperature. The reaction was heated with reflux for 2 hours and stirred over night at room temperature. After hydrolysis with 5 ml of iced water (subsequent stirring for 1 hour), the reaction was shaken with CHCl₃/MeOH (3:2). The organic phase was dried over $Na_2SO_4$, rotated and dissolved in 15 ml of CHCl₃, 10 ml of acetonitrile and 5 ml of iso-propanol. Then, 1.5 g of a trimethylamine solution (33% in ethanol) were added. The reaction flask was tigthly sealed and stirred over night at 50° C. The reaction solution was rotated, taken up by 5 ml of CHCl₃ and shaken twice with each of 4 ml of formic acid/MeOH (5:7), 4 ml of sodium acetate (0.1 M)/MeOH (5:7) and 3 ml of sodium chloride (1 M)/MeOH (5:7). Drying over NaSO₄ and column chromatography of the organic phase yielded 99 mg (38%) of the desired compound.

M ($C_{45}H_{60}N_2O_8{}^{31}P$)=773 g/mol

FAB-MS (FAB⁺, NBA): m/z=796.3 [M+Na], 774.4 [MH⁺], 601.5, 569.4, 531.4, 413.3, 215.1. HR -FAB ($C_{45}H_{61}O_8NP$): calc.: 774.4145; found: 774.4135. HR-FAB ($C_{45}H_{60}O_8NPNa$): calc.: 796.3954; found: 796.3951. ¹H-NMR (CD₃OD): δ (ppm)=8.34-7.89 (9H, m, $CH_{arom}$), 7.73-7.45 (5H, m, $CH_{arom}$), 5.41-5.37 (1CH, m, CH), 4.20-4.17 (2H, m, $CH_2N$), 4.05-3.35 (14H, m, 4 $OCH_2$, $CH_2OP$, POCH$_2$, CH$_2$C$_{16}$H$_9$), 3.16 (9H, s, 3 CH$_3$), 1.96-1.90 (2H, m, CH$_2$), 1.81-1.72 (2H, m, CH$_2$), 1.52-1.48 (4H, m, 2 CH$_2$), 1.28 (12H, m, 6 CH$_2$). $^{13}$C-NMR (CD$_3$OD): δ (ppm)= 167.78 (1 CO), 138.30-124.60 (14 CH$_{arom}$, 8 C$_{arom}$), 74.27 (1 CH), 72.81-70.48 (4 CH$_2$O), 68.87, 66.90, 60.95 (1 CH$_2$N, 1 CH$_2$OP, 1 POCH$_2$), 54.90 (3 CH$_3$), 34.38-27.29 (11 CH$_2$).

1-O-{(10-[4-(pyrene-1-yl)-butoxy]-decyl}-rac-glycero-3-phosphocholine 90 mg (0.12 mmol) of 1-O-{10-[4-(pyrene-1-yl)-butoxy]-decyl}-2-O-benzoyl-rac-glycero-3-phosphocholine were dissolved in 3 ml of MeOH, and 1.5 ml of a 0.1 M Bu$_4$NOH solution was added thereto in MeOH (1.25 eq). The reaction solution was concentrated after 2 hours. Column chromatography yielded 71 mg (90%) of the lyso-compound.

M (C$_{38}$H$_{56}$NO$_7$$^{31}$P)=669 g/mol

FAB-MS (FAB$^+$, NBA): m/z=692.3 [M+Na], 670.4 [MH$^+$], 669.4 [M], 584.3, 242.3, 289.1, 215.1. HR-FAB (C$_{38}$H$_{57}$NO$_7$$^{31}$P): calc.: 670.3873; found: 670.3881. HR-FAB (C$_{38}$H$_{56}$NO$_7$$^{31}$PNa): calc.: 692.3692; found: 692.3693. $^1$H-NMR (CD$_3$OD): δ (ppm)=8.23-7.88 (9H, m, CH$_{arom}$), 4.43-4.38 (2H, m, CH$_2$N), 4.02-3.36 (15H, m, 4 OCH$_2$, OCH, CH$_2$OP, POCH$_2$, CH$_2$C$_{16}$H$_9$), 3.22 (9H, s, 3 CH$_3$), 1.96-1.87 (2H, m, CH$_2$), 1.77-1.66 (2H, m, CH$_2$), 1.55-1.47 (4H, m, 2 CH$_2$), 1.27 (12H, m, 6 CH$_2$). $^{13}$C-NMR (CDCl$_3$): δ (ppm)=170.46 (1 CO), 138.16-124.48 (9 CH$_{arom}$, 7 C$_{arom}$), 72.90-71.47 (4 CH$_2$O), 71.03 (1 CH), 67.31, 66.63, 59.33 (1 CH$_2$OP, 1 CH$_2$N, 1 POCH$_2$), 54.78 (3 CH$_3$), 33.36-24.59 (10 CH$_2$). IR (KBr): ṽ (cm$^{-1}$)=3418s, 3039m, 2852m, 1635m, 1490m, 1467m, 1375w, 1230m, 1111m, 1087m, 1051m, 970m, 928w, 850m.

1O-{10-[4-pyrene-1 yl)-butoxy]decyl}-2-(6-(2,4dinitrophenyl)-aminohexoyl)-rac-glycero-3-phosphocholine 0.326 g (1.1 mmol) of 6-(2,4-dinitrophenylamino)-hexane acid, 136 mg (0.66 mmol) of DCC and 408 mg (3.2 mmol) of DMAP were added to 0.150 g (0.22 mmol) of 1-O-{10-[4-(pyrene-1-yl)-butoxyl]-decyl}-rac-glycero-3-phosphocholine in 10 ml of dichloromethane and stirred for 40 hours at room temperature. To the resulting suspension 5 ml of water were then added and filtered over kieselguhr. After separation of the phases and chromatography, 56 mg (26%) of the product were isolated.

M (C$_{50}$H$_{69}$N$_4$O$_{12}$$^{31}$P)=948 g/mol

FAB-MS (FAB$^+$, NBA): m/z=971.4 [M+Na], 949.4 [MH$^+$], 884.4, 862.4, 721.4, 243.2, 215. 1. HR-FAB (C$_{50}$H$_{70}$O$_{12}$N$_4$P): calc.: 949.4725; found: 949.4755. HR-FAB (C$_{50}$H$_{69}$O$_{12}$N$_4$PNa): calc.: 971.4545; found: 971.4547. $^1$H-NMR (CDCl$_3$): δ (ppm)=9.00-6.67 (12H, m, CH$_{arom}$), 5.13-5.10 (1H, m, CH), 4.34-4.28 (2H, m, CH$_2$N), 4.08-3.23 (16H, m, 4 OCH$_2$, POCH$_2$, CH$_2$OP, CH$_2$N, CH$_2$Cl$_{16}$H$_9$), 3.18 (9H, s, 3 CH$_3$), 2.38-2.31 (2H, m, CH$_2$CO), 1.95-1.86 (4H, m, 2, CH$_2$), 1.80-1.72 (2H, m, CH$_2$), 1.56-1.41 (8H, m, 4 CH$_2$), 1.25 (12H, m, 6 CH$_2$). $^{13}$C-NMR (CDCl$_3$): δ (ppm)=170.46 (1 CO), 148.66-113.98 (12 CH$_{arom}$, 10 C$_{arom}$), 73.86 (1 CH), 72.81-69.12 (4 CH$_2$O), 67.31, 66.63, 60.30 (1 CH$_2$OP, 1 CH$_2$N, 1 POCH$_2$), 54.78 (3 CH$_3$), 43.27 (1 CH$_2$N), 33.36-24.59 (1 CH$_2$CO, 14 CH$_2$) IR (KBr): ṽ (cm$^{-1}$)=3365m, 3107w, 3042w, 2928m, 2853m, 1729m, 1623s, 1589m, 1525m, 1500w, 1475w, 1425m, 1369w, 1337s, 1312m, 1280m, 1245m, 1187m, 1144m, 1094m, 1060w, 1032w, 923w, 832w, 745w.

EXAMPLE 2

Determination of the Activity of PAF-AH Using 1-O-{10-[4-(pyrene-1-yl)-butoxy]-decyl}-2-(6-(2,4-dinitrophenyl)-aminohexoyl)-rac-glycero-3-phosphocholine According to the Invention For the examinations, 10 mM of DMSO stock solution of the compound according to the invention of Example 1 were prepared and then respectively diluted with the buffer of use (0.1 M TRIS HCl, 0.1% Tween20, pH 7.4) at the desired concentrations for the respective tests.

Measurements in a Quartz Cuvette

Use is made of quartz cuvettes (1 cm×1 cm) of Helma (Müllheim/Baden, Germany) with a volume of 1 ml.

Settings in the Cary Eclipse software of Varian (Darmstadt, Germany):

In the kinetics module: Ex. Wavelength (nm)=344.00; Em. Wavelength (nm)=377.00; Ex. Slit (nm)=5; Em. Slit (nm)=5; Averaging Time (s)=0.1000; Dwell time (s)=0.1000; Cycle time (min)=0.2500; Excitation filter=Auto; Emission filter=Open; Multicell holder=Multicell; PMT voltage (V)=Medium; Temperature control.

The examinations were carried out using a four-way Peltier cuvette holder at 37° C.

Measurements in a Microtiter Plate

Use was made of white 96-well titer plates of Perkin Elmer (Überlingen, Germany) and black 96-well FIA plates of Greiner (Frikenhausen, Germany).

Settings in the Cary Eclipse software of Varian (Darmstadt, Germany):

In the kinetics module: Ex. Wavelength (nm)=344.00; Em. Wavelength (nm)=377.00; Ex. Slit (nm)=5; Em. Slit (nm)=5; Averaging Time (s)=0.1000; Cycle time (min)=0.0000; Excitation filter=Auto; Emission filter=Open; PMT voltage (V)=Medium; Wellplate=ON; Read position=Well centre.

Preparation of PAF-AH

Preparation and Purity Examination of Plasma and Human LDL

Buffer used: PBS buffer (150 mM NaCl, 40 mM phosphate, 1 mM EDTA, pH=7.4). The buffer was saturated with argon for 15 min.

Preparation of Plasma 100 ml of freshly collected, heparinized blood was centrifuged for 10 min in 2×50 ml tubes at room temperature, using a Hermle centrifuge at 3,000 rpm. 20 ml were taken from each supernatant, pooled, 400 µl of 0.1 M EDTA solution (pH=7.45) added thereto, and stratified with argon.

Preparation of LDL 12.2112 g of KBr p.a. was added to 32 ml of the plasma sample and stratified with argon. The KBr was dissolved by slow oscillation. 2 ml of the PBS solution were prepared in 6×4 ml centrifuge tubes of Beckman (Munich, Germany) and the plasma sample, with KBr added thereto, was added to form a layer. This was then centrifuged at 4° C. and at 37,000 rpm in a vacuum for 2 hours. After this time, the centrifuge tubes were carefully removed from the rotor.

The desired LDL is distinguishable as a yellow band, at a distance of about ⅓ from the bottom of the centrifuge tube. At first, the upper white layer was removed and discarded. The yellow layer is about 1 mm thick. Said layer was removed using a blunt, bent needle. The LDL contained in all 6 centrifuge tubes was pooled and stratified with argon. In order to remove the KBr, 300 µl of the thus obtained solution were chromatographed by means of a Sephadex-G25 minicolumn using PBS buffer.

Protein Measurement

Solution A: 1% $Na_2BCA$, 2% $Na_2CO_3$ $H_2O$, 0.16% $Na_2$tartrate, 0.4% NaOH, 0.95% $NaHCO_3$, pH=11.25

Solution B: 4% $CuSO_4$ 5 $H_2O$

BSA was used as the standard; all measurements were carried out as double measurements. The total volume of one preparation was 300 µl/well, and usually 2.5 µl of the sample to be determined (after dilution, as the case may be) were employed. This was filled up to 75 µl with water, and 225 µl of a 50:1 mixture of solution A and solution B were added thereto. The incubation time was 2 hours at room temperature. The samples were then photometrically measured at 562 nm.

Examination of the Purity of the Isolated LDL

The examination was carried out using submaritime mini gel electrophoresis.

Gel composition: 20 ml of barbital buffer (50 mM, pH=8.6), 0.3% Separide™ (60 mg)

Preparation of the isolated LDL: 10 µl (0.5-1 µg) of columned LDL, 0.5 µl of 9-diethylamino-5H[a]phenoxazene-5-one (Nile Red) (0.4 mg/ml), 10 µl of application buffer (TBE buffer, 30% glycerol, 1% SDS, spatula tip of Bromphenol Blue)

TBE buffer (89 mM TRIS HCl, 89 mM $B(OH)_3$, 2 mM EDTA, pH=8.5)

Duration of electrophoresis: 1 h (at a constant U of 56 V) at room temperature

Fixing solution: 25% $^i$PrOH, 10% acetic acid, 65% water

Staining solution: 50% MeOH, 10% acetic acid, 40% water, 0.05% Coomassie Brilliant Blue R 250

Destaining solution: 5% MeOH, 7% acetic acid, 88% water

Isolation of PAF-AH from LDL

Buffer A: 25 mM TRIS HCl, 0.1% Tween20, 2 mM EDTA, pH 7.6

Buffer B: 25 mM TRIS HCl, 0.1% Tween20, 2 mM EDTA, 50-200 mM NaCl, pH 7.6 (linear gradient)

All work was carried out at 4° C.

1 ml (2 mg/ml) LDL was pipetted onto a pre-equilibrated (Buffer A) DEAE Sepharose® FF chromatography column of Amersham Pharmacia biotech (Freiburg, Germany) and washed with 6 times the column filling volume to give the protein-free eluent. Next, the protein was eluated with buffer B. The highest PAF-AH activity was obtained with fractions of 100-150 mM NaCl. These were pooled and concentrated by ultrafiltration (Amicon YM30). The upgraded fractions were then pipetted onto a pre-equilibrated (Buffer A) Blue Sepharose® 6FF chromatography column of Amersham Pharmacia biotech (Freiburg, Germany) and washed with 6 times the column filling volume to give the protein-free eluent. Next, the protein was eluated with buffer A+0.5 M NaCl. The fractions having the highest PAF-AH activity were pooled and concentrated by ultrafiltration (Amicon YM30).

The content of PAF-AH was determined by protein determination. Purity was examined by analogy with the SDS electrophoresis of LDL. The resulting PAF-AH was sufficiently pure for activity examinations.

The invention claimed is:

1. A compound of formula (1)

$$F-L_1-O-CH_2$$
$$HC-O-L_2-Q$$
$$H_2C-O-P(=O)(O^-)-O-(CH_2)_2-N^+(CH_3)_3 \quad (1)$$

wherein
$L_1$ comprises an ether $(R^1-OR^2)_m$, wherein $R^1$ and $R^2$ are independently selected from a hydrocarbon having 1 to 12 carbon atoms, with m being an integer from 1 to 4, or from a hydrocarbon R having 1 to 20 carbon atoms, and wherein a carbon atom of $L_1$ is bonded to an sn-1 positioned O atom;
F comprises pyrene as a fluorophore;
Q is a quencher, and
$L_2$ is C(O)-$L_1$ or C(O)-$L_1$-NH, wherein $L_1$ is as defined above.

2. The compound of claim 1, wherein the quencher comprises a 2,4-dinitrophenyl residue.

3. The compound of claim 1, wherein $R^1$ and $R^2$ are independently selected as $(CH_2)_n$ and a is an integer from 2 to 12.

4. The compound of claim 1, wherein $L_1$ is $(CH_2)_4$—O—$(CH_2)_{10}$.

5. The compound of claim 1, wherein R is $(CH_2)_o$ and o is an integer from 1 to 20.

6. The compound of claim 1, wherein $L_2$ is C(O)—$(CH_2)_p$ or C(O)—$(CH_2)_p$—NH and p is an integer from 1 to 20.

7. The compound of claim 6, wherein $L_2$ is C(O)—$(CH_2)_5$—NH.

8. The compound of claim 1, wherein said compound has the structure of:

[pyrene]—$(CH_2)_4O(CH_2)_{10}$—O—$CH_2$
HC—O—C(=O)—$(CH_2)_5$—NH—[2,4-dinitrophenyl]
$H_2C$—O—P(=O)($O^-$)—O—$(CH_2)_2$—$N^+(CH_3)_3$ 9. The compound of claim 1, wherein F is a substituted pyrene.

10. A method for detecting activity of phospholipase $A_2$, present in a solution, comprising reacting the solution with a compound having the formula $$F-L_1-O-CH_2$$
$$HC-O-L_2-Q$$
$$H_2C-O-P(=O)(O^-)-O-(CH_2)_2-N^+(CH_3)_3$$

wherein $L_1$ comprises an ether $(R^1-OR^2)_m$, wherein $R^1$ and $R^2$ are independently selected from a hydrocarbon having 1 to 12 carbon atoms, with m being an integer from 1 from 4, or from a hydrocarbon R having 1 to 20 carbon atoms, and wherein a carbon atom of $L_1$ is bonded to an sn-1 positioned O atom;
F comprises nyrene as a fluorophore;
O is a quencher,
$L_2$ is C(O)—$L_1$ or C(O)-$L_1$-NH, wherein $L_1$ is as defined above; and detecting activity of phospholipase $A_2$ by measuring the level of fluorescence intensity of the fluorophore in the solution.

11. The method of claim 10, wherein the quencher comprises a 2,4-dinitrophenyl residue.

12. The method of claim 10, wherein $R^1$ and $R^2$ are independently selected as $(CH_2)_n$ and n is an integer from 2 to 12.

13. The method of claim 10, wherein R is $(CH_2)_o$ and o is an integer from 1 to 20.

14. The method of claim 10, wherein $L_2$ is C(O)—$(CH_2)_p$ or C(O)—$(CH_2)_p$—NH and p is an integer from 1 to 20.

15. The method of claim 10, wherein $L_2$ is C(O)—$(CH_2)_5$—NH.

16. The method of claim 10, wherein said compound has the structure of:

17. The method of claim 10, wherein the phospholipase A$_2$ is Platelet-Activating Factor Acetylhydrolase.

* * * * *